United States Patent
Chaudhuri et al.

(10) Patent No.: US 6,649,150 B2
(45) Date of Patent: Nov. 18, 2003

(54) SKIN-LIGHTENING

(75) Inventors: Ratan K. Chaudhuri, Lincoln Park, NJ (US); Francois Marchio, Scarsdale, NY (US)

(73) Assignees: EM Industries, Hawthorne, NY (US); Natreon Inc., New Brunswick, NJ (US)

( * ) Notice: Subject to any disclaimer, the term of this patent is extended or adjusted under 35 U.S.C. 154(b) by 0 days.

(21) Appl. No.: 10/120,156

(22) Filed: Apr. 11, 2002

(65) Prior Publication Data

US 2003/0198612 A1 Oct. 23, 2003

(51) Int. Cl.$^7$ .......................... A61K 7/135; A61K 35/78
(52) U.S. Cl. .......................... 424/62; 424/769; 424/777
(58) Field of Search ................................ 424/769, 777, 424/62; 435/810

(56) References Cited

U.S. PATENT DOCUMENTS

| | | |
|---|---|---|
| 5,073,545 A | 12/1991 | Arima et al. |
| 5,078,989 A | 1/1992 | Ando et al. |
| 5,145,781 A | 9/1992 | Suzuki et al. |
| 5,609,875 A | 3/1997 | Hadas |
| 5,824,327 A * | 10/1998 | Whittemore et al. |
| 6,066,312 A | 5/2000 | Egawa et al. |
| 6,124,268 A | 9/2000 | Ghosal |
| 6,235,721 B1 * | 5/2001 | Ghosal |
| 6,362,167 B1 * | 3/2002 | Ghosal |

FOREIGN PATENT DOCUMENTS

FR    2730408    8/1996

OTHER PUBLICATIONS

Budavari et al., The Merck Index: An Encylopedia of Chemicals, Drugs, and Biologicals, 11th Edition, 1989, Merck & Co., Inc., Rahway, NJ.*
Halliwell, Free Radical Research, 25, 439–54 (1996).
Ghosal et al., Indian Journal of Chemistry, 35B, Sep. 1996, pp. 941–948.
Chemical Abstract 126:255293, "Maillard reaction inhibitors containing tannin (hydrozylates), and skin–lightening and antiaging cosmetics containg them" (1997).
Chemical Abstract 73:42386, "Hydrolyzable tannins of Eucalyptus delegatensis wood" (1970).

* cited by examiner

Primary Examiner—Christopher R. Tate
Assistant Examiner—Michele Flood
(74) Attorney, Agent, or Firm—Millen, White, Zelano & Branigan, P.C.

(57) ABSTRACT

A light colored standardized extract of Emblica officinalis consisting essentially of over 40% by weight of Emblicanin A. Emblicanin B, Pedunculagin and Punigluconin, and not more than about 1% by weight of flavonoids, and methods of producing same. Also disclosed are cosmetic or pharmaceutical compositions comprising the standardized extract and methods of using same to lighten or whiten skin.

26 Claims, No Drawings

SKIN-LIGHTENING

FIELD OF THE INVENTION

This invention relates to novel skin lightening or whitening or even toning compositions and methods of administering same for their pharmaceutical, cosmetic and aesthetic applications.

BACKGROUND OF THE INVENTION

As stated in the scientific literature, the type and amount of melanin synthesized by the melanocyte and its distribution pattern in the surrounding keratinocytes determines the actual color of the human skin. Melanin forms through a series of oxidative reactions involving the amino acid tyrosine in the presence of the enzyme tyrosinase. The first step is the most critical because the remainder of the reaction sequences can proceed spontaneously at physiological pH. Thus, tyrosinase converts tyrosine to dihydroxyphenylalanine (DOPA) and then to dapaquinone. Subsequently, dopaquinone converted to dopachrome, through autooxidation, and finally to dihydroxyindole or dihydroxyindole-2-carboxylic acid (DHICA) to form eumelanin (brown-black pigment). The later reaction occurs in the presence of dopachrome tautomerase and DHICA oxidase. In the presence of cysteine or glutathione, dopaquinone is converted to cysteinyl DOPA or glutathione DOPA. Subsequently, pheomelanin, a yellow-red pigment, is formed.

The color of the skin and its intensity therefore depend on the rate of formation of the melanin, its degree of polymerization, the speed of exfoliation and the thickness of the horny layer, i.e. the layer that contains the most pigment. For a more detailed discussion of the pigmentation pathway, attention is invited to "Skin Depigmenting Agents", Michael P. Tabibran M.D., (Medicine Journal, Jul. 8, 2001, Vol. 2, November 7.)

In general, to reduce cutaneous pigmentation, it is necessary to reduce the rate of formation of the melanin by inhibiting the tyrosinase while retarding its polymerization and accelerating the exfoliation of the horny layer.

For purposes of skin lightening or whitening or even toning, topical application of skin lightening or whitening or even toning agent should have a lightening, whitening or even toning effect on the only area to be treated, produce neither irritation nor post-inflammatory secondary pigmentation, and cause neither a systemic depigmenting effect nor an allergic reaction.

In addition, the skin lightening, whitening or even toning should be effective for normal cutaneous pigmentation and its excesses: including but not limited to lentigo senilis, chloasma, hyperpigmentation after use of photosensitizing products, and cicatrical brown spots.

In French patent 2730408 published Aug. 14, 1996, compositions are proposed to regulate cutaneous pigmentation, based on extracts of fruits among which is *Phyllantus emblica* (syn.*Emblica officinalis*). The composition may be based on a dilute-alcoholic extract obtained from the *Phyllantus emblica* or an extract obtained, for example by merely pressing the fruit.

Both the extracts obtained by pressing and the extracts obtained by alcoholic maceration may then be concentrated at a moderate temperature under reduced pressure, preferably less than 50° C., then optionally brought to the dry state by freeze-drying or any other method under reduced pressure and at a temperature that is lower than 50° C. so as to avoid degrading the active ingredients of the fruit. In greater detail, examples 3, 6 and 8 of the French patent 2730408 illustrate the manufacture and uses of extracts based on *Phyllantus emblica*.

In this French patent, however, there is no indication of the composition or the chemical nature of the extracts being defined. Conversely, in U.S. Pat. No. 6,124,268, Ghosal, issued Sep. 26, 2000 entitled "Natural Oxidant Compositions, Method For Obtaining Same And Cosmetic, Pharmaceutical and Nutritional Formulations Thereof" there is set forth the chemical composition of extracts of *Emblica officinalis* obtained by extracting the fresh fruit at elevated temperatures; e.g. 70° C., using a very dilute aqueous or alcoholic-water salt solution, e.g. 0.1 to 5%. By this extraction process, in the presence of sodium chloride, for example, hydrolysis of the glycocidic enzymes in the plant is prevented and the product is protected from microbial infestation.

In the Ghosal patent, the antioxidant blend of the constituents is described under the name of "CAPROS", with claim 8, for example, of the patent setting forth the composition as follows:

An antioxidant blend consisting of, by weight, (1) and (2) about 35–55% of the gallic/ellagic acid derivatives of 2-keto-glucono-δ-lactone; (3) about 4–15% of 2,3-di-O-galloyl-4, 6-(S)-hexahydroxydiphenoylgluconic acid; (4) about 10–20% of 2,3,4,6-bis-(S)-hexahydroxydiphenoyl-D-glucose; (5) about 5–15% of 3',4',5,7-tetrahydroxyflavone-3-O-rhamnoglucoside; and (6) about 10–30% of tannoids of gallic/ellagic acid.

The common names of the enumerated compounds are (1) and (2) Emblicanin A and Emblicanin B, (3) Punigluconin, (4) Pedunculagin and (5) Rutin. There is no mention of its utility as a skin lightening or whitening or even toning agent has been indicated by Ghosal.

With respect to acceptability of the products of the French and U.S. Patents for the purposes of skin whitening, they have one or more disadvantages.

An object of the present invention, therefore, is to provide a novel composition and method for whitening or lightening or even toning skin for the above described cosmetic and dermatological indications among others.

Upon further study of this application, other objects and advantages of the invention will become apparent.

SUMMARY

It has been discovered that a closely related but novel standardized antioxidant composition based on an extract of *Emblica officinalis* provides a more acceptable skin whitening composition and method of use.

The antioxidant composition used in the present invention comprises a modification of the CAPROS composition, comprising a standardized extract of low molecular weight (<1000) hydrolyzable tannins, over 40%, preferably 50–80% w/w of Emblicanin A, Emblicanin B, Pedunculagin, and Punigluconin with low levels (<1%, w/w) of total flavonoids whereby the resultant products of the invention can be made into elegant white to off-white formulations. Such a composition is discussed with greater specificity in pages 28–30 of the Aug. 2001 issue of Soap, Perfumery and Cosmetics, the article having the title Ingredients/Emblica, Bearing Fruit, by Ratan K. Chaudhuri. In that article there is no mention, however, of any flavonoids much less the maximum acceptable amounts in the composition.

According to the present invention, the total flavonoids are maintained at a level which does not impair the desired color, e.g. generally, by weight, less than about 1.0%, preferably less than about 0.8%, and even more preferably less than about 0.6%. In comparison, commercial competitive products have significantly higher contents of total flavonoids and exhibit a significantly darker color. Also, the desired concentrations of the Rutin species of flavonoids (3',4',5',7-tetrahydroxyflavone-3-0-rhamnoglucoside) in the standardized extract are less than 1.0%, less than 0.01%, less than 0.001% and less than 0.0001%, with a value of 0.01 to 0.001% being particularly preferred. The most preferred concentrations of the components are on a percent by weight basis of the total dried extract:

| Product Identity | Most Preferred Concentrations % by weight |
|---|---|
| Emblicanin A | 20–35 |
| Emblicanin B | 10–20 |
| Pedunculagin | 15–30 |
| Punigluconin | 3–12 |
| Total Flavonoids | <1 |

The standardized composition may exhibit average percentage deviations from these preferred values of:

| Product Identity | Preferred Deviation | Most Preferred Deviation |
|---|---|---|
| Emblicanin A | ±10% | ±5% |
| Emblicanin B | ±10% | ±5% |
| Pedunculagin | ±10% | ±5% |
| Punigluconin | ±10% | ±5% |
| Total Flavonoids | ±10% | ±5% |

The antioxidant composition can be obtained by removal of the total flavonoids by reversed-phase column chromatography or HPLC using a solvent system of acetonitrile, water/phosphoric acid (20/80/1) or other solvent combinations as they elute faster than the low molecular-weight tannins. Also, by selection of geographical location, the *Phyllanthus emblica* fruit extract may provide a substantially lower level of the total flavonoids (<1.0%). It has been observed that medium-sized fruits collected from some parts of eastern India, during October-November, after water extraction and drying, yielded the preferred antioxidant composition as a powder with the desired low content of total flavonoids. Accordingly, by analyzing the total flavonoids content of extracts and selecting such extracts that contain the desired low content of total flavonoids, it is possible to prepare a standardized extract.

In the context of the present invention "flavonoids" include a family of compounds which exhibit a peak at 350 nm when analyzed by UV spectral data. Examples of flavonoids include but are not limited to flavonols and flavones, a species thereof being Rutin as discussed above.

In general, the standardized extract is sold as a powder in packaged form, e.g. in drums, in amounts of generally at least 500 g, with samples weighing about 50 g. Larger or smaller commercial shipments are also possible, the only proviso being that the powder in the package has been analyzed and conforms to the above tabulated specifications. In order to obtain the packaged powder with the desired specifications, an optional process comprises blending different batches of powdered extract, with at least one batch being below specification, but with the blend meeting specifications.

The resultant standardized extract powdery material is then incorporated in a cosmetically or pharmaceutically acceptable carrier, preferably having a pH of about between 3 to 6.5. The carrier is any conventional carrier for topical administration and is preferably employed in a concentration of about 90% to 99.7%, preferably 95 to 99.5. (In other words, the concentration of the antioxidant composition of the present invention is generally about 0.3 to 10% by weight, preferably 0.5 to 5% by weight.)

In addition to or included with the above mentioned disorders for which this invention can be of use, are without limitation: freckles reduction, reduction of yellow mass-tone on Asians skins and inhibition of skin Dischromia related to the aging process, as well as a reduction in redness linked to venous disorders and a reduction in UV-induced pigmentation.

The antioxidant composition and formulation of the present invention can be optionally mixed with other skin whitening agents, either known prior to the present disclosure as well as those which will be invented in the future. For example, the skin whitening products which can be combined include but are not limited to cysteine, 4-thioresorcin, 3-aminotyrosine, 5-hydroxy-2-hydroxymethyl-γ-pyridone, fomesjaponicus and ganoderma extracts, kojic acid, glabridin, liqorice extract, glycyrrhizinic acid, hydroquinone-β-glucoside, catharanthus roseus extract, proteoglycans, proteinase inhibitors, oligopeptides, betaines, and methyl 4-benzyloxy-2-hydroxybenzoate and 4-benzyloxy-2-hydroxybenzoic acid.

In addition to skin whitening activity, the compositions and formulations of the present invention are effective photoprotective agents and can be optionally blended with other photoprotective agents.

As for the optional photoprotective agents, if sunscreens are added, suitable sunscreens include any agent capable of protecting the skin from UV radiation including, for example, butyl methoxydibenzoylmethane, cinoxate, benzophenone-8, homosalate, menthyl anthranilate, octocrylene, ethyhexyl methoxycinnamate, ethylhexyl salicylate, benzophenone-3, ethylhexyl dimethyl PABA, glyceryl PABA, phenylbenzimidazole sulfonic acid, benzophenone4, ethyhexyl triazone, diethylhexyl butamido triazone, bisimidazylate etc.

For the purposes of providing a topical formulation with the active compound or compounds of the present invention, any of the known topical excipients can be used therewith such as mineral oils, emulsifying agents, preservatives, anti-oxidants, skin penetrants, etc., including but not limited to the various topical excipients which are utilized in the Ghosal patent U.S. Pat. No. 6,124,268 and the references discussed above. The compositions can be employed as a typical topical compositions employed in the dermatological and cosmetic field, e.g., lotions, gels, emulsions, sprays, sticks, liposomes, etc.

With respect to the amount of the topical composition which is applied to the skin, it should be a sufficient amount and for a sufficient period of time to visibly whiten the skin.

Preferably the topical composition contains an amount of 0.3 to 5.0% by weight of the inventive composition in a formulated product and preferably for at least about once per day for a period of preferably at least about two weeks.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications, cited above or below is hereby incorporated by reference.

Examples of lotions include but are not limited to the following formulations:

TABLE 1

Moisturizing Lotion with 0.5% Emblica ™

| INCI NAME | % w/w |
| --- | --- |
| Phase A-1 | |
| Water (demineralized) | 59.15 |
| Disodium EDTA | 0.05 |
| Propylene Glycol | 5.00 |
| Phase A-2 | |
| Xantham Gum | 0.20 |
| Phase B | |
| PEG-6 stearate, ceteth-20, glyceryl stearate, steareth-20, stearic acid | 10.00 |
| Stearic Acid | 1.00 |
| Hydrogenated castor oil | 1.00 |
| Octyldodecyl myristate | 8.00 |
| Dimethicone | 4.00 |
| Phenyltrimethicone | 2.00 |
| Sweet Almond oil | 3.00 |
| Phase C | |
| Water (demineralized) | 5.00 |
| *Phyllanthus emblica* fruit extract | 0.50 |
| Phase D | |
| Triethanolamine | 0.10 |
| Phase E | |
| Phenoxyethanol, Isopropylparaben, Isobutylparaben, Butylparaben | 1.00 |
| Total | 100.00 |

Procedure

Disperse A-2 in A-1 and heat to 70–75° C. Combine B and heat to 70–75° C. Add B to A while stirring. Homogenize until mixture cools to 60° C. At 30° C. add phase C. Adjust pH with TEA to 5.0–6.0. Add phase E. Mix until uniform.

TABLE 2

Lotion with 0.5% Emblica ™

| INCI NAME | % w/w |
| --- | --- |
| Phase A | |
| Water (demineralized) | 66.61 |
| Disodium EDTA | 0.10 |
| Propylene Glycol | 2.00 |
| Sorbitol | 2.00 |
| Sodium Lauryl Sulfate | 0.15 |
| Phase B | |
| Glyceryl stearate | 5.00 |
| Stearic acid | 1.00 |
| *Persea Gratissima* (Avocado) oil Unsaponifiables | 15.00 |
| Beeswax | 1.50 |
| Phase C | |
| Water (demineralized) | 5.00 |
| *Phyllanthus emblica* fruit extract | 0.50 |
| Phase D | |
| Triethanolamine | 0.14 |
| Phase E | |
| Propylene glycol, DMDM Hydantoin, Methylparaben | 1.00 |
| Total | 100.00 |

Procedure

Combine A and heat to 70–75° C. Combine B and heat to 70–75° C. Add B to A while stirring. Add phase C at 30° C. Adjust pH to 5.0–6.0 with phase D. Add phase E. Mix until uniform.

TABLE 3

Lotion with Emblica ™ (O/W)

| INCI NAME | % w/w |
| --- | --- |
| Phase A | |
| *Paraffinum Liquidum* (Mineral Oil) | 8.00 |
| Trilaureth-4 Phosphate | 1.50 |
| Polyglyceryl-2 Sesquiisostearate | 2.00 |
| Isopropyl Palmitate | 6.00 |
| Octyl Stearate | 5.00 |
| Carbomer | 0.40 |
| Phase B | |
| Glycerin | 3.00 |
| Preservatives | q. s. |
| Water (demineralized) | 68.60 |
| Phase C | |
| Water (demineralized) | 5.00 |
| *Phyllanthus emblica* fruit extract | 0.50 |
| Phase D | |
| Triethanolamine | q. s. |
| Total | 100.00 |

Procedure

Mix phases A and B separately. Add phase B into A. Add phase C. Neutralize with phase D.

Homogenize.

Note

PH=6.00

Viscosity 5200 mPa.s (Brookfield RVT, T-B, 10 rpm)

TABLE 4

Lotion with 1.0% Emblica ™

| INCI NAME | % w/w |
| --- | --- |
| Phase A | |
| Water (demineralized) | 65.97 |
| Disodium EDTA | 0.10 |
| Propylene Glycol | 2.00 |
| Sorbitol | 2.00 |
| Sodium Lauryl Sulfate | 0.15 |

TABLE 4-continued

Lotion with 1.0% Emblica ™

| INCI NAME | % w/w |
|---|---|
| Phase B | |
| Glyceryl stearate | 5.00 |
| Stearic acid | 1.00 |
| *Persea Gratissima* (Avocado) oil Unsaponifiables | 15.00 |
| Beeswax | 1.50 |
| Phase C | |
| Water (demineralized) | 5.00 |
| *Phyllanthus emblica* fruit extract | 1.00 |
| Phase D | |
| Triethanolamine | 0.28 |
| Phase E | |
| Propylene glycol, DMDM Hydantoin, Methylparaben | 1.00 |
| Total | 100.00 |

Procedure
Combine A and heat to 70–75° C. Combine B and heat LO 70–75° C. Add B to A while stirring. Add phase C at 30° C. Adjust pH to 5.0–6.0 with phase D. Add phase E. Mix until uniform.

TABLE 5

Skin Lightening Lotion

| INCI NAME | % w/w |
|---|---|
| Phase A-1 | |
| Water (demineralized) | 55.05 |
| Disodium EDTA | 0.05 |
| Propylene Glycol | 5.00 |
| Phase A-2 | |
| Xantham Gum | 0.25 |
| Magnesium aluminum stearate | 0.40 |
| Phase B | |
| Cetearyl alcohol and cetearyl glucoside | 7.00 |
| Apricot kernel oil | 10.00 |
| Octyl stearate | 3.00 |
| Dimethicone | 6.00 |
| Phase C | |
| Water (demineralized) | 10.00 |
| *Phyllanthus emblica* fruit extract | 2.00 |
| Phase D | |
| Triethanolamine | 0.25 |
| Phase E | |
| Phenoxyethanol, Isopropylparaben Isobutylparaben, Butylparaben | 1.00 |
| Phase F | |
| Fragrance | 0.25 |
| Total | 100.00 |

Procedure
Disperse A-2 in A-1 and heat to 70–75° C. Combine B and heat to 70–75° C. Add B to A while stirring. Homogenize until mixture cools to 60° C. At 30° C. add phase C. Adjust pH with TEA to 4.0–5.0. Add phase E. Add F. Mix until uniform.

TABLE 6

Skin Lightening Lotion

| INCI NAME | % w/w |
|---|---|
| Phase A-1 | |
| Water (demineralized) | 56.18 |
| Disodium EDTA | 0.05 |
| Propylene Glycol | 5.00 |
| Phase A-2 | |
| Xantham Gum | 0.25 |
| Magnesium aluminum stearate | 0.40 |
| Phase B | |
| Cetearyl alcohol and cetearyl glucoside | 7.00 |
| Apricot kernel oil | 10.00 |
| Octyl stearate | 3.00 |
| Dimethicone | 6.00 |
| Phase C | |
| Water (demineralized) | 10.00 |
| *Phyllanthus emblica* fruit extract | 1.00 |
| Phase D | |
| Triethanolamine | 0.12 |
| Phase E | |
| Phenoxyethanol Isopropylparaben Isobutylparaben, Butylparaben | 1.00 |
| Phase F | |
| Fragrance | 0.25 |
| Total | 100.00 |

Procedure
Disperse A-2 in A-1 and heat to 70–75° C. Combine B and heat to 70–75° C. Add B to A while stirring. Homogenize until mixture cools to 60° C. At 30° C. add phase C. Adjust pH with TEA to 4.0–5.0. Add phase E. Add F. Mix until uniform.

TABLE 7

Lotion with 0.2% Emblica
Formulation # EUS 18-87

| INCI name | % w/w |
|---|---|
| Phase A | |
| Water (demineralized) | 60.73 |
| Na2 EDTA | 0.05 |
| Propylene Glycol | 5.00 |
| Phase B | |
| PEG-6 Stearate and Ceteth-20 and Glyceryl Stearate and Steareth-20 | 10.00 |
| Glyceryl Stearate and PEG-100 Stearate | 6.00 |
| Stearyl alcohol | 3.00 |
| Dimethicone | 4.00 |
| Phase C | |
| Water (demineralized) | 10.00 |
| *Emblica oficinalis* fruit extract | 0.20 |
| Phase D | |
| Triethanolamine | 0.02 |
| Phase E | |
| Phenoxyethanol and Isopropylparaben and Isobutylparaben and Butylparaben | 1.00 |
| Total | 100.00 |

Procedure
Combine A and heat to 70–75° C.
Combine B and heat to 70–75° C.
Add B to A under agitation.
Homogenize mixture.
Add C at 40° C.
Adjust pH to 4.0–5.0 with D.
Add E. Mix until mixture reaches RT.

TABLE 8

Lotion with 0.5% Emblica
Formulation # EUS 18-89

| INCI name | % w/w |
|---|---|
| Phase A | |
| Water (demineralized) | 60.39 |
| Na2 EDTA | 0.05 |
| Propylene Glycol | 5.00 |
| Phase B | |
| PEG-6 Stearate and Ceteth-20 and Glyceryl Stearate and Steareth-20 | 10.00 |
| Glyceryl Stearate and PEG-100 Stearate | 6.00 |
| Stearyl alcohol | 3.00 |
| Dimethicone | 4.00 |
| Phase C | |
| Water (demineralized) | 10.00 |
| *Emblica oficinalis* fruit extract | 0.50 |
| Phase D | |
| Triethanolamine | 0.06 |
| Phase E | |
| Phenoxyethanol and Isopropylparaben and Isobutylparaben and Butylparaben | 1.00 |
| Total | 100.00 |

Procedure
Combine A and heat to 70–75° C.
Combine B and heat to 70–75° C.
Add B to A under agitation.
Homogenize mixture.
Add C at 40° C.
Adjust pH to 4.0–5.0 with 0.
Add E. Mix until mixture reaches RT.

COMPARISON OF PREFERRED VERSUS COMMERCIAL COMPOSITIONS

In the following tables there are presented representative analyses of components of Applicants' products versus commercial products, and also a table which compares the absorbances of Applicants' product versus the commercial products. The latter table is important for it demonstrates that products of the invention have a lighter color and can be formulated into aesthetically superior products than the commercial extracts. As such, the following tables are self-explanatory.

TABLE I

Percentage Total Flavonoids (% w/w) Present in the Product of Present Invention vs. Commercial Products

| Examples | Supplier | Lot Number | % Flavonoids |
|---|---|---|---|
| 1 | Present Invention | CA 0107009 | 0.93 |
| 2 | Present Invention | CA 0107010 | 0.91 |
| 3 | Present Invention | CA0107011 | 0.84 |
| 4 | Present Invention | CA 0107012 | 0.88 |
| 5 | Present Invention | 8001 | 0.46 |
| 6 | Present Invention | KAMJ-544 | 0.68 |
| 7 | Ayush Herbs, Inc., USA | Ay/Amla/00461 | 7.77 |
| 8 | Geni, Inc., USA* | AML-01 | 2.75 |
| 9 | Geni, Inc., USA | AME-T1 | 4.06 |
| 10 | Geni, Inc., USA | AME-T2 | 3.41 |
| 11 | Rose Color, Inc., USA | R-8 | 1.91 |
| 12 | Tripple Crown America, Inc. USA | EO-0525 | 3.02 |
| 13 | Tripple Crown America, Inc. USA | EO-0792 | 2.7 |
| 14 | Tripple Crown America, Inc. USA | EO-1584 | 2.89 |

Method of Analysis

Quantification of total flavonoids was done using Rutin as an external standard and by calculating % area of peaks.

Solvent system: Acetonitrile:Water Phosphoric acid (20:80:1)

Flow rate: 0.8 ml/mim

Column: Merck-Hilbar® Prepacked Column RT 250-4, LiChrosorb® RP-18

Detection: UV detector at 350 nm

TABLE II

Percentage Total Low Molecular-Weight (<1,000) Tannins Present in the Product of Present Invention vs. Commercial Products

| Supplier | Lot Number | % Low Molecular-Weight Tannins in the Product |
|---|---|---|
| Present Invention | CA 0012006 | 75.48 |
| Present Invention | CA 0107010 | 72.94 |
| Present Invention | CA0106007 | 75.48 |
| Present Invention | CA0008002 | 67.53 |
| Present Invention | 4001 | 67.73 |
| Ayush Herbs, Inc., USA | Ay/Amla/00461 | 9.03 |
| Geni, Inc., USA* | AML-01 | 44.17 |
| Geni, Inc., USA | AME-T1 | 17.20 |
| Geni, Inc., USA | AME-T2 | 18.00 |
| Rose Color, Inc., USA | R-8 | 23.40 |
| Tripple Crown America, Inc. USA | EO-0525 | 29.60 |
| Tripple Crown America, Inc. USA | EO-0792 | 28.91 |
| Tripple Crown America, Inc. USA | EO-1584 | 29.49 |

TABLE III

Percentage Low Molecular-Weight (<1,000) Tannins Present in the Product of Present Invention vs. Commercial Products

| Product Lot Number | Emblicanin A | Emblicanin B | Punigluconin | Pedunculagin |
|---|---|---|---|---|
| CA 0012006 | 22.47 | 17.11 | 10.16 | 25.73 |
| CA 0107010 | 26.59 | 14.86 | 10.32 | 21.17 |
| CA0106007 | 27.95 | 16.36 | 8.20 | 24.81 |
| CA0008002 | 21.84 | 16.29 | 7.61 | 21.79 |
| 4001 | 29.32 | 14.91 | 4.79 | 18.72 |
| Ay/Amla/00461 | 4.55 | 2.30 | 1.92 | 0.27 |
| AML-01* | 18.10 | 12.14 | 9.43 | 4.50 |

TABLE III-continued

Percentage Low Molecular-Weight (<1,000) Tannins Present
in the Product of Present Invention vs. Commercial Products

| Product Lot Number | Emblicanin A | Emblicanin B | Punigluconin | Ped-unculagin |
|---|---|---|---|---|
| AME-T1 | 8.27 | 2.93 | 3.11 | 2.88 |
| AME-T2 | 8.58 | 3.07 | 3.23 | 3.12 |
| R-8 | 9.79 | 7.94 | 5.31 | 0.36 |
| EO-0525 | 9.94 | 9.25 | 9.49 | 0.92 |
| EO-0792 | 9.21 | 9.78 | 8.83 | 1.09 |
| EO-1584 | 10.35 | 9.29 | 8.78 | 1.08 |

*This product is very dark and difficult to formulate with due to a large amount of water-insoluble polymeric tannins. The relatively light colored products of this invention have a relatively small amount of such water-insoluble polymeric tannins and as such, they do not materially affect the advantages of the invention, namely the desired light color and relative ease of formulations.

Accordingly, preferred subgeneric aspects of this invention include but are not limited to standardized extracts having an absorbance (optical density) of 0.8 maximum in the UV region at wavelength 350 nm and/or a maximum of 0.3 in the UV region at wavelength 410 nm and/or a maximum of 0.1 nm in the UV region at wavelength 470 nm and/or a 0.08 maximum in the UV region at wavelength 530 nm, and/or a maximum of 0.09 in the UV region at wavelengths 590 nm and/or a maximum of 0.02 in the UV region at wavelength 650 nm. Thus, comprehensive embodiments of standardized extracts as related to absorbances are those standardized extracts having 2, 3, 4, 5 or 6 of the above absorbances, with the most comprehensive having in the UV region a maximum optical density of 0.8 at wavelength 350 nm, a maximum optical density of 0.3 at wavelength 410 nm, a maximum optical density of 0.1 at wavelength 470 nm, a maximum optical density of 0.08 at wavelength 530 nm, a maximum optical density of 0.09 at wavelength 590 nm and a maximum optical density of 0.02 at wavelength 650 nm.

TABLE IV

Comparative Color Profile of Products Obtained from the Present Invention vs. Commercially Available Products

| No. | Supplier | Lot Number | Absorbance (optical density) at different wavelengths ($\lambda$) | | | | | |
|---|---|---|---|---|---|---|---|---|
| | | | 350 | 410 | 470 | 530 | 590 | 650 |
| 1 | Present Invention | CA 0107009 | .621 | .152 | .037 | .033 | .012 | .004 |
| 2 | Present Invention | CA 0107010 | .644 | .153 | .036 | .028 | .020 | .004 |
| 3 | Present Invention | CA 0107011 | .604 | .140 | .036 | .020 | .004 | .004 |
| 4 | Present Invention | CA 0107012 | .530 | .124 | .019 | .012 | .005 | .002 |
| 5 | Present Invention | CA 0008002 | .595 | .196 | .063 | .035 | .021 | .021 |
| 6 | Present Invention | CA 0012006 | .558 | .180 | .048 | .024 | .012 | .006 |
| 7 | Ayush Herbs, Inc., USA | Ay/Amla/00461 | >2.25 | 1.43 | .692 | .396 | .285 | .248 |
| 8 | Geni, Inc., USA* | AML-01 | >2.25 | 1.08 | .600 | .375 | .250 | .175 |
| 9 | Geni, Inc., USA | AME-T1 | >2.25 | 1.27 | .540 | .311 | .195 | .150 |
| 10 | Geni, Inc., USA | AME-T2 | >2.25 | 1.29 | .680 | .448 | .332 | .274 |
| 11 | Rose Color, Inc., USA | R-8 | >2.25 | .999 | .148 | .074 | .351 | .036 |
| 12 | Tripple Crown America, Inc. USA | EO-0525 | >2.25 | 1.15 | .672 | .474 | .364 | .276 |
| 13 | Tripple Crown America, Inc. USA | EO-0792 | >2.25 | 1.73 | 1.05 | .776 | .606 | .504 |
| 14 | Tripple Crown America, Inc. USA | EO-1584 | >2.25 | 1.33 | .800 | .575 | .475 | .35 |

Method of Analysis

Test compounds (0.5 g) were weighed and dissolved in distilled water (100 ml) by sonicating for 10 min to give a final concentration of 0.5% (w/v). The resulting solution was filtered and the absorbance was recorded between $\lambda$350 to 650 nm, against distilled water in a DU-64 Spectrophotometer.

Results

Six samples (# 1–6) of the present invention clearly exhibit much less absorbance values at the six different wavelengths (350–650 nm) determined in the study. All other samples (# 7–14) exhibit much higher absorbance values at the respective wavelengths studied than any other samples of the present invention.

Conclusion

The study clearly indicates the color intensity of competitive materials is five to over ten times higher in the wavelengths studied. Formulated products containing these materials is found to be much darker (unacceptable to consumers and have limited shelf life) color even at low concentrations (~0.1%) whereas formulated products prepared using the material of the present invention have much better color at any level (~0.1 to 3% level).

CLINICAL EXAMPLE

Thirteen Hispanic and thirteen Asian human volunteers were treated with a test formulation tabulated on the following page entitled "Formulation Used For Clinical Testing (EMBLIC®)".

The test formulation was applied to both the right and left upper arms of the volunteers at a rate of 0.05 ml twice daily for 12 weeks. The results were represented using the individual typology angle (COLIPA SPF test method); measured by chromometric measurement.

TABLE 9

FORMULATION USED FOR CLINICAL TESTING (EMBLICA ®)
Formulation # EUS 17-99 (2% Emblica)

| INCI name | % w/w | 1.75 kg |
|---|---|---|
| Phase A | | |
| Water (demineralized) | 58.70 | 1027.25 |
| Na2 EDTA | 0.05 | 0.88 |
| Propylene Glycol | 5.00 | 87.50 |

TABLE 9-continued

FORMULATION USED FOR CLINICAL TESTING (EMBLICA ®)
Formulation # EUS 17-99 (2% Emblica)

| INCI name | % w/w | 1.75 kg |
|---|---|---|
| Phase B | | |
| PEG-6 Stearate and Ceteth-20 and Glyceryl Stearate and Steareth-20 | 10.00 | 175.00 |
| Glyceryl Stearate and PEG-100 Stearate | 6.00 | 105.00 |
| Stearyl alcohol | 3.00 | 52.50 |
| Dimethicone | 4.00 | 70.00 |
| Phase C | | |
| Water (demineralized) | 10.00 | 175.00 |
| *Phyllanthus emblica* fruit extract | 2.00 | 35.00 |
| Phase D | | |
| Triethanolamine | 0.25 | 4.38 |
| Phase E | | |
| Phenoxyethanol and Isopropylparaben and Isobutylparaben and Butylparaben | 1.00 | 17.50 |
| Total | 100.00 | 1750.00 |

The preceding examples can be repeated with similar success by substituting the generically or specifically described reactants and/or operating conditions of this invention for those used in the preceding examples.

The entire disclosure of all applications, patents and publications, cited above or below, are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A standardized light colored skin-lightening or whitening powder consisting essentially of by weight: 20–35% Emblicanin A, 10–20% Emblicanin B, 15–30% Pedunculagin and 3–12% Punigluconin 0.001 to 0.01% by weight of Rutin, less than about 1% flavonoids, said weight percentages having an average deviation of not more than 10%.

2. A powder according to claim 1, wherein the average percentage deviation is not more than 5%.

3. A standardized powder according to claim 1, wherein the powder weighs at least 500 g and is in packaged form.

4. A standardized powder according to claim 2, wherein the powder weighs at least 500 g and is in packaged form.

5. A white to off white formulation comprising a standardized powder according to claim 1 and a cosmetically or pharmaceutically acceptable carrier.

6. A white to off white formulation according to claim 5, wherein the content of said carrier is about 90–99.7% by weight.

7. A formulation according to claim 5, further comprising a skin-lightening or whitening agent chemically different from said standardized powder.

8. A formulation according to claim 5, further comprising a photoprotective agent chemically different from said standardized powder.

9. A standardized powder according to claim 1 having an absorbance (optical density) of 0.8 maximum in the UV region length at wavelength 350 nm.

10. A standardized powder according to claim 1 having an absorbance (optical density) of 0.3 maximum in the UV region length at wavelength 410 nm.

11. A standardized powder according to claim 1 having an absorbance (optical density) of 0.1 maximum in the UV region length at wavelength 470 nm.

12. A standardized powder according to claim 1 having an absorbance (optical density) of 0.08 maximum in the UV region length at wavelength 530 nm.

13. A standardized powder according to claim 1 having an absorbance (optical density) of 0.09 maximum in the UV region length at wavelength 590 nm.

14. A standardized powder according to claim 1 having an absorbance (optical density) of 0.02 maximum in the UV region length at wavelength 650 nm.

15. A standardized powder according to claim 1 having maximum absorbance (optical density) in the UV region length of 0.8 at wavelength 410 nm, 0.1 at wavelength 470 nm, 0.08 at wavelength 530 nm, 0.09 at wavelength 590 nm, and 0.02 at wavelength 650 nm.

16. A standardized powder according to claim 15, wherein the powder weighs at least 500 g and is in packaged form.

17. A white to off white formulation comprising a standardized powder according to claim 15 and a cosmetically or pharmaceutically acceptable carrier.

18. A standardized light colored skin-lightening or whitening powder consisting essentially of over 40% by weight of Emblicanin A, Emblicanin B, Pedunculagin and Punigluconin and less than about 1% by weight of flavonoids.

19. A standardized powder according to claim 18 consisting essentially of by weight 50–80% of Emblican A, Emblican B, Pedunculagin and Punigluconin and less than about 0.6% by weight of flavonoids.

20. A standardized light colored skin-lightening or whitening powder according to claim 18, consisting essentially of by weight: 20–35% Emblicanin A, 10–20% Emblicanin B, 15–30% Pedunculagin and 3–12% Punigluconin, Rutin in an amount of not more than 1%, and less than about 1% flavonoids, said weight percentages having an average deviation of 10%.

21. A standardized powder according to claim 18 having maximum absorbances (optical density) in the UV region of 0.8 at wavelength 410 nm, 0.1 at wavelength 470 nm, 0.08 at wavelength 530 nm, 0.09 at wavelength 590 nm, and 0.02 at wavelength 650 nm.

22. A standardized powder according to claim 19 having maximum absorbances (optical density) in the UV region of 0.8 at wavelength 410 nm, 0.1 at wavelength 470 nm, 0.08 at wavelength 530 nm, 0.09 at wavelength 590 nm, and 0.02 at wavelength 650 nm.

23. A standardized powder according to claim 20 having maximum absorbances (optical density) in the UV region of 0.8 at wavelength 410 nm, 0.1 at wavelength 470 nm, 0.08 at wavelength 530 nm, 0.09 at wavelength 590 nm, and 0.02 at wavelength 650 nm.

24. A powder according to claim 18 containing not more than about 0.6% by weight of flavonoids.

25. A powder according to claim 19 containing not more than about 0.6% by weight of flavonoids.

26. A powder according to claim 20 containing not more than about 0.6% by weight of flavonoids.

* * * * *